United States Patent
Zhang et al.

(10) Patent No.: US 9,997,266 B2
(45) Date of Patent: Jun. 12, 2018

(54) PROTECTIVE DEVICE AND LASER RAMAN SAFETY INSPECTION APPARATUS COMPRISING THE SAME

(71) Applicant: NUCTECH COMPANY LIMITED, Beijing (CN)

(72) Inventors: Li Zhang, Beijing (CN); Shixin Zhang, Beijing (CN); Lin Yang, Beijing (CN); Hongqiu Wang, Beijing (CN); Yumin Yi, Beijing (CN); Huacheng Feng, Beijing (CN); Jianhong Zhang, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 0 days. days.

(21) Appl. No.: 15/273,881

(22) Filed: Sep. 23, 2016

(65) Prior Publication Data

US 2017/0186506 A1 Jun. 29, 2017

(30) Foreign Application Priority Data

Dec. 28, 2015 (CN) .......................... 2015 1 1001493

(51) Int. Cl.
| | |
|---|---|
| G21F 5/12 | (2006.01) |
| G01N 21/65 | (2006.01) |
| G01J 3/02 | (2006.01) |
| F16P 3/08 | (2006.01) |
| G01J 3/44 | (2006.01) |
| G01N 21/35 | (2014.01) |

(52) U.S. Cl.
CPC .................. *G21F 5/12* (2013.01); *F16P 3/08* (2013.01); *G01J 3/0291* (2013.01); *G01J 3/44* (2013.01); *G01N 21/65* (2013.01); *G01N 21/35* (2013.01); *G01N 2201/0225* (2013.01)

(58) Field of Classification Search
CPC .. G01N 23/04; H05G 1/02; G01T 7/08; G21F 1/00; G21F 3/00
USPC ............................................ 250/505.1, 515.1
See application file for complete search history.

(56) References Cited

U.S. PATENT DOCUMENTS

| | | | |
|---|---|---|---|
| 2005/0108945 A1 | 5/2005 | Wiemer et al. | |
| 2006/0076322 A1 | 4/2006 | Brauchle et al. | |

(Continued)

FOREIGN PATENT DOCUMENTS

| | | |
|---|---|---|
| CN | 200959105 Y | 10/2007 |
| CN | 101974997 A | 2/2011 |

(Continued)

OTHER PUBLICATIONS

Notification of the 1st Office Action dated Jan. 25, 2017, for the corresponding Chinese Patent Application No. 201511001493.1.

(Continued)

*Primary Examiner* — Nicole Ippolito
(74) *Attorney, Agent, or Firm* — Morgan, Lewis & Bockius LLP

(57) ABSTRACT

Embodiments of the present invention provide a protective device including a sliding door and a housing, together forming a closed space, wherein, a guide rail is provided on the housing, and the sliding door is slidable along the guide rail to open or close the closed space. In addition, embodiments of the present invention also provide a laser Raman safety inspection apparatus including the abovementioned protective device.

9 Claims, 2 Drawing Sheets

(56) References Cited

U.S. PATENT DOCUMENTS

| | | | |
|---|---|---|---|
| 2007/0096856 A1 | 5/2007 | Wiemer et al. | |
| 2010/0111266 A1* | 5/2010 | Kuhnmuench | G21F 7/005 378/203 |
| 2010/0267049 A1* | 10/2010 | Rutter | G01N 21/6428 435/7.1 |
| 2012/0127317 A1* | 5/2012 | Yantek | G01V 8/14 348/156 |
| 2012/0255955 A1 | 10/2012 | Nolan | |

FOREIGN PATENT DOCUMENTS

| | | |
|---|---|---|
| CN | 202640003 U | 1/2013 |
| CN | 203287320 U | 11/2013 |
| CN | 103466182 A | 12/2013 |
| CN | 203405415 U | 1/2014 |
| CN | 203509362 U | 4/2014 |
| CN | 203549349 U | 4/2014 |
| CN | 204071160 U | 1/2015 |
| CN | 204081860 U | 1/2015 |
| CN | 204507723 U | 7/2015 |
| CN | 205256948 U | 5/2016 |
| EP | 1526239 A1 | 4/2005 |
| EP | 2 161 150 A2 | 3/2010 |

OTHER PUBLICATIONS

Communication with Extended European Search Report dated Dec. 23, 2016 in corresponding European Patent Application No. 16190943.7.

Communication from European Patent Office dated Mar. 14, 2018 regarding corresponding European Patent Application No. 16 190 943.7.

* cited by examiner

PROTECTIVE DEVICE AND LASER RAMAN SAFETY INSPECTION APPARATUS COMPRISING THE SAME

CROSS-REFERENCE TO RELATED APPLICATION

This application claims the benefit of Chinese Patent Application No. 201511001493.1 filed on Dec. 28, 2015 in the State Intellectual Property Office of China, the whole disclosure of which is incorporated herein by reference.

BACKGROUND

1. Technical Field

Embodiments of the present invention relate to the field of laser Raman spectroscopy-based safety inspection technology, and particularly to a protective device and a laser Raman safety inspection apparatus comprising the protective device.

2. Description of the Related Art

In prior art, a laser Raman spectrometer is usually adopted to inspect dangerous goods and perform substance identification, and, visible laser or infrared laser is used as its light source to irradiate a substance to be inspected to obtain Raman spectrum scattered by the substance. The Raman spectrum is only related to molecular structure of the substance to be inspected, and thus can be regarded as "fingerprint" information for identification of the substance to be inspected. Accordingly, through the Raman spectrum, structural information of substance can be obtained, which can determine category of the substance.

Visible laser or infrared laser will cause permanent damage to retina or other human tissues after reaching a certain power. So, when an apparatus with laser irradiation is adopted, its inspection device is required to satisfy safety requirements and should not cause laser irradiation damage to operator(s) on-site.

However, conventional apparatus has poor sealing performance, which results in leakage of visible laser or infrared laser, causing harm to human body.

In addition, since safety inspection apparatus is normally used in crowded areas including airports, rail transportation, customs, important venues and the like, it should have high detection efficiency, in order to avoid crowd congestion. Nevertheless, conventional apparatus has generally low efficiency.

SUMMARY

According to one aspect of the present invention, there is provided a protective device including a sliding door and a housing, together forming a closed space, wherein, a guide rail is provided on the housing, and the sliding door is slidable along the guide rail to open or close the closed space.

According to another aspect of the present invention, there is provided a laser Raman safety inspection apparatus comprising the abovementioned protective device.

Exemplary embodiments of the present invention will be described hereinafter in detail with reference to the attached drawings.

BRIEF DESCRIPTION OF THE DRAWINGS

These and/or other objects and advantages of the present invention will become apparent and more readily appreciated from the following description of the embodiments, taken in conjunction with the accompanying drawings of which.

DETAILED DESCRIPTION OF THE EMBODIMENTS

Figure 1:
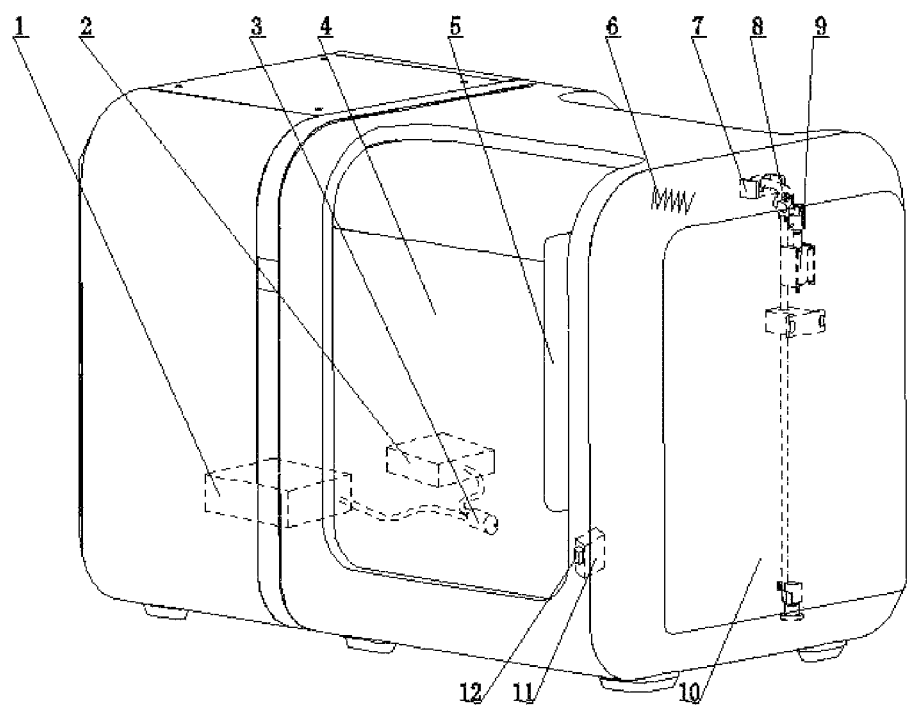
FIG. 1 is a schematic view of a laser Raman safety inspection apparatus according to an embodiment of the present invention.

Embodiments of the present invention will be described hereinafter in detail with reference to the attached drawings, wherein the like reference numerals refer to the like elements. The present invention may, however, be embodied in many different forms and should not be construed as being limited to the embodiment set forth herein; rather, these embodiments are provided so that the present invention will be thorough and complete, and will fully convey the concept of the present invention to those skilled in the art.

Figure 2:
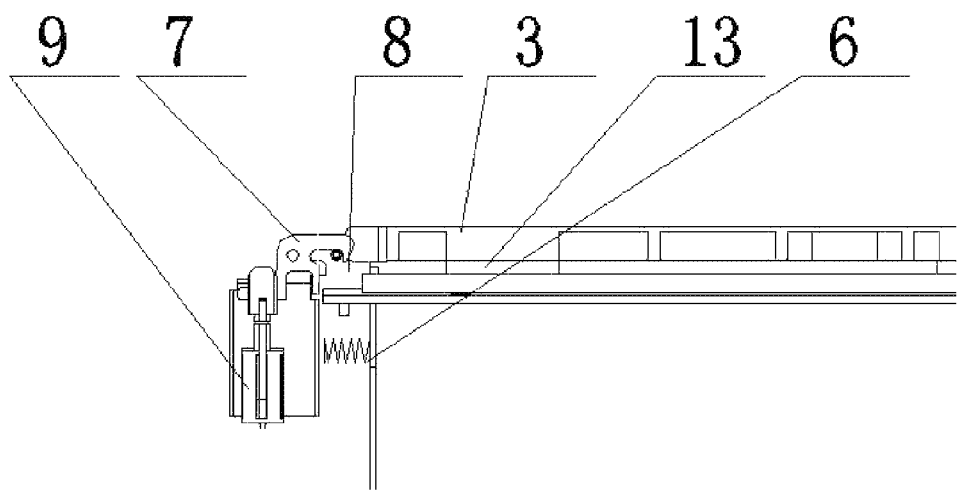
FIG. 2 is a partial schematic view of the laser Raman safety inspection apparatus shown in FIG. 1.

FIGS. 1-2 shows schematic views of a laser Raman safety inspection apparatus including a protective device according to an embodiment of the present invention. In particular, referring to FIGS. 1-2, the laser Raman safety inspection apparatus comprises a Raman spectrometer 1, a laser device 2 and a laser probe 3. The protective device according to embodiments of the present invention comprises a sliding door 4 and a housing 10, together forming a closed space. A guide rail 13 is provided on the housing 10, and the sliding door 4 is slidable along the guide rail 13 to open or close the closed space.

The Raman spectrometer 1, the laser device 2 and the laser probe 3 are provided within the closed space. When the laser Raman safety inspection apparatus performs a safety inspection, the closed space is closed, avoiding leakage of visible laser or infrared laser. Accordingly, the protective device according to embodiments of the present invention improves safety performance of the laser Raman safety inspection apparatus.

According to an embodiment of the present invention, the sliding door and the housing are made of light-tight material. As a result, safety performance of the laser Raman safety inspection apparatus is further improved.

After a safety inspection operation is completed, the closed space is opened through a sliding operation of the sliding door. An object to be inspected can be taken out from the closed space, and then a next object to be inspected can be put into the closed space. Through another sliding operation of the sliding door, the closed space is closed, continuing to perform a new safety inspection operation.

In order to improve efficiency of the safety inspection operation, in an embodiment of the present invention, the sliding door comprises sliding doors respectively located at two sides. In this way, taking out and putting in actions of the objects to be inspected can be performed at both the sliding doors, improving efficiency of the safety inspection operation. Specifically, during a safety inspection operation, once the closed space is opened, an operator stayed at a left side can take out an object on which a safety inspection operation has been done from the closed space at the left side, while another operator stayed at a right side can put an object to be inspected into the closed space at the right side. The above two actions can be performed at the same time, which improves efficiency of the safety inspection operation. In addition, in this embodiment of the present invention, sliding doors at both sides are used as the sliding door, which effectively improves applicability of the apparatus, for example, the safety inspection apparatus can be operated either at its left side or at its right side, reducing its requirements on on-site inspection occupied space and environments.

In order to further improve safety performance of the safety inspection apparatus, in an embodiment of the present invention, as shown in FIG. 1, the sliding door is provided with a first locking element 7 and the housing is provided with a second locking element 8. The first locking element 7 is engaged and locked with the second locking element 8 when the closed space formed by the sliding door and the housing is closed; and the first locking element 7 is disengaged and unlocked from the second locking element 8 when the closed space formed by the sliding door and the housing is to be opened.

The first locking element 7 may be provided at a middle part of the sliding door, and correspondingly, the second locking element 8 is provided at a corresponding part of the housing. Mechanical manner or electromagnetic manner may be adopted for engagement and locking between the first locking element and the second locking element, and, other suitable locking manner may be adopted in accordance with practical requirements. In addition, positional relationship between the first locking element and the second locking element is not limited to that mentioned in the above embodiment of the present invention. The first locking element and the second locking element may be positioned in any other suitable locations so long as they can be engaged and locked with each other when the closed space formed by the sliding door and the housing is closed.

In an embodiment of the present invention, as shown in FIGS. 1-2, an electromagnetic unit 9 is provided to apply an electromagnetic force to lock the first locking element 7 and the second locking element 8 with each other. Specifically, when the closed space formed by the sliding door and the housing is closed, the electromagnetic unit 9 applies an electromagnetic force to lock the first locking element 7 and the second locking element 8 with each other. When the closed space formed by the sliding door and the housing is to be opened, namely when the safety inspection apparatus emits no more visible laser or infrared laser after the safety inspection operation is completed, the safety inspection apparatus sends a signal to the electromagnetic unit 9, to remove the electromagnetic force applied on the first locking element 7 and the second locking element 8, so as to release the locking therebetween.

With the above configuration, possibility of leakage of visible laser or infrared laser can be further avoided. It should be noted that, the above configuration is exemplary only, and for those skilled in the art, other suitable configuration for achieving locking and unlocking between the first locking element and the second locking element may be adopted.

In order to further improve safety performance of the safety inspection apparatus, in an embodiment of the present invention, as shown in FIGS. 1-2, the sliding door is provided with a sensor 12 and the housing is provided with a sense switch 11. When the closed space formed by the sliding door and the housing is closed, the sense switch is triggered by the sensor to send a signal; and, when the closed space is opened, the sense switch is triggered to send another signal again. Upon receiving the signal from the sense switch, the safety inspection apparatus determines that the closed space formed by the sliding door and the housing has been closed, and emits visible laser or infrared laser to perform a safety inspection on the object to be inspected. When the safety inspection apparatus receives again another signal from the sense switch, the safety inspection apparatus determines that the closed space formed by the sliding door and the housing has been opened, and emits no more visible laser or infrared laser.

With the above configuration, safety performance of the safety inspection apparatus is further improved.

It should be noted that, for those skilled in the art, the aforementioned embodiments can be used separately or in combination. For example, both or only one of the above-mentioned electromagnetic unit and the sensing unit can be included in the protective device. In case that both of them are included, a double security performance is achieved. In other words, these aforementioned embodiments do not limit the present invention, and for those skilled in the art, these aforementioned embodiments can be used separately or in combination.

In order to further improve convenience of the operation of the protective device, in the aforementioned embodiment where the locking unit is included, the protective device is further configured that, the housing is provided with an elastic element 6. As shown in FIG. 2, the elastic element 6 is compressed by the sliding door when the closed space formed by the sliding door and the housing is closed. When the locking between the first locking element and the second locking element are released, the sliding door slides under the action of a restoring force of the elastic element 6, to open the closed space.

The elastic element comprises coil spring, belleville spring or linear spring.

Once a safety inspection operation is completed, the safety inspection apparatus sends a signal to the electromagnetic unit 9 to release the locking between the first locking element 7 and the second locking element 8, and due to existence of the abovementioned elastic element, the sliding door slides automatically under the action of the restoring force of the elastic element to open the closed space.

In order to facilitate convenient use of the protective device, in an embodiment of the present invention, a handle 5 is provided on the sliding door.

In addition, embodiments of the present invention also provide a laser Raman safety inspection apparatus including the abovementioned protective device.

The above description is merely used to illustrate exemplary embodiments of the present invention, but not to limit the present invention. For example, configurations of and relatively positional relationship between the sliding door and the housing can be changed or modified. Also for example, technical features in different embodiments can be combined. It should be understood by those skilled in the art that, all of changes, equivalent alternatives, modifications, made within principles and spirit of the present invention, should be included within the scope of the present invention.

What is claimed is:

1. A protective device for laser safety inspection, the protective device comprising:
   a sliding door and a housing, together forming a closed space,
   wherein, a guide rail is provided on the housing, and the sliding door is slidable along the guide rail to open or close the closed space;
   wherein, the sliding door comprises two sliding doors that are provided at opposing sides of the housing, respectively, such that picking-out and/or placing-in of an object to be inspected can be done at each side simultaneously.

2. The protective device of claim 1, wherein, the sliding door is provided with a first locking element and the housing is provided with a second locking element, wherein, the first locking element is engaged and locked with the second locking element when the closed space formed by the sliding door and the housing is closed; and the first locking element is disengaged and unlocked from the second locking element when the closed space formed by the sliding door and the housing is to be opened.

3. The protective device of claim 2, wherein, the housing is provided with an elastic element, wherein, the elastic element is compressed by the sliding door when the closed space formed by the sliding door and the housing is closed; and, when the first locking element is disengaged and unlocked from the second locking element, the sliding door slides under the action of a restoring force of the elastic element, to open the closed space.

4. The protective device of claim 1, wherein, the sliding door is provided with a sensor and the housing is provided with a sense switch; wherein, when the closed space formed by the sliding door and the housing is closed, the sense switch is triggered by the sensor to send a signal; and, when the closed space is opened, the sense switch is triggered to send another signal again.

5. The protective device of claim 2, wherein, locking/unlocking between the first locking element and the second locking element is achieved by means of an electromagnetic force.

6. The protective device of claim 1, wherein, a handle is provided on the sliding door.

7. The protective device of claim 1, wherein, the sliding door and the housing are made of light-tight materials.

8. The protective device of claim 3, wherein, the elastic element comprises coil spring, belleville spring or linear spring.

9. A laser Raman safety inspection apparatus comprising the protective device of claim 1.

\* \* \* \* \*